United States Patent [19]

Boden et al.

[11] Patent Number: 5,136,018
[45] Date of Patent: Aug. 4, 1992

[54] MACROCYCLIC POLYARYLATE COMPOSITIONS OF DECREASED CRYSTALLINITY

[75] Inventors: Eugene P. Boden, Scotia; Peter D. Phelps, Schenectady, both of N.Y.

[73] Assignee: General Electric Company, Schenectady, N.Y.

[21] Appl. No.: 615,942

[22] Filed: Nov. 19, 1990

[51] Int. Cl.[5] ............... C08G 63/82; C08G 63/00; C08G 63/02; C08G 67/00
[52] U.S. Cl. .................... 528/357; 528/176; 528/190; 528/271; 528/272; 528/274; 528/279; 528/298; 528/355
[58] Field of Search ............... 528/176, 190, 271, 272, 528/274, 279, 298, 355, 357

[56] References Cited

U.S. PATENT DOCUMENTS

| | | | |
|---|---|---|---|
| 4,757,132 | 7/1988 | Brunelle et al. | 528/176 |
| 4,829,144 | 5/1989 | Brunelle et al. | 528/190 |
| 4,853,457 | 8/1989 | Joyce | 528/190 |
| 4,927,904 | 5/1990 | Guggenheim et al. | 528/182 |

*Primary Examiner*—John Kight, III
*Assistant Examiner*—T. Mosley
*Attorney, Agent, or Firm*—William H. Pittman; James C. Davis, Jr.

[57] ABSTRACT

Macrocyclic polyarylate oligomers containing a mixture of isophthalate and terephthalate moieties are prepared by reaction of a mixture of isophthaloyl and terephthaloyl chloride with one or more bisphenols under specific reaction conditions. They are characterized by a reduced degree of crystallinity and therefore lower processing temperatures than the corresponding isophthalate oligomers.

14 Claims, No Drawings

MACROCYCLIC POLYARYLATE COMPOSITIONS OF DECREASED CRYSTALLINITY

This invention relates to macrocyclic polyarylate oligomers, and more particularly to oligomer compositions having improved processability.

The preparation of macrocyclic polyester oligomers is described, for example, in U.S. Pat. Nos. 4,757,132 and 4,927,904, the disclosures of which are incorporated by reference herein. They have certain advantages as intermediates for linear polyarylate preparation. For example, they may be employed in reactive processing operations such as resin transfer molding, being capable of liquefaction before transfer to the mold wherein they undergo polymerization to the desired linear polyarylates.

The principal known cyclic polyarylate oligomers are esters of bisphenols with various individual aromatic dicarboxylic acids, particularly isophthalic acid and terephthalic acid. They are similar in their capabilities and potential utilities to the cyclic polycarbonate oligomers disclosed, for example, in U.S. Pat. No. 4,644,053.

They differ, however, in the distributions of oligomer species of various degrees of polymerization. Macrocyclic polycarbonate oligomer mixtures of the type conventionally prepared generally contain a roughly statistical distribution of oligomers of varying degrees of polymerization. In such a distribution, the trimer and tetramer are present in relatively large amounts and higher oligomers in progressively smaller amounts, with the compounds having degrees of polymerization from 2 to about 12 constituting essentially all of the oligomer mixture.

In macrocyclic polyarylate oligomers such as the bisphenol A isophthalate, on the other hand, the cyclic trimer is by far the predominant species in the mixture. Tetramers, pentamers and higher oligomers are present, but only in quite small proportions compared to the proportion thereof found in the cyclic polycarbonates. The cyclic trimer is frequently present in trace amounts in linear polyarylate resins prepared from cyclic oligomers.

One result of this oligomer distribution is that relatively high processing temperatures are required for the macrocyclic polyarylate oligomer compositions. Cyclic bisphenol A isophthalate trimer melts above 400° C., and the oligomer mixtures generally obtained require temperatures greater than 350° C. to be fully melted. It is believed that one reason for the requirement of such high temperatures is the high proportion of crystalline species with high melting points, such as the aforementioned trimer.

It has now been discovered that the crystallinity of cyclic polyarylate oligomer mixtures is substantially reduced when a substantial proportion (i.e., about 2-50% by number) of the molecular species present therein are terephthalate species. The incorporation of terephthalate moieties causes a change in distribution of the species present, producing a relatively large number and relatively large amounts of numerous species having differing degrees of polymerization. One result is a decrease in the melting point and consequently an improvement in processing conditions. Another is the formation of linear polyarylates of low crystallinity and concomitant high processability.

Accordingly, the invention is a macrocyclic polyarylate oligomer composition comprising molecules of the formula

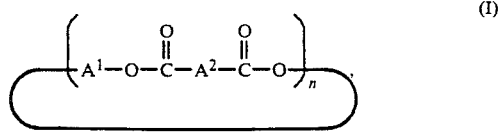

wherein $A^1$ is

or

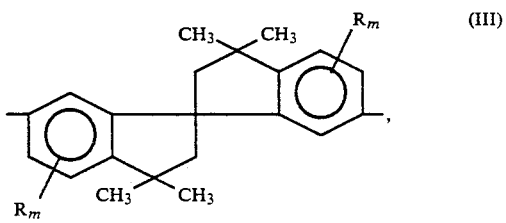

about 2-65% of the $A^2$ moieties are p-phenylene and the remainder are m-phenylene, Y is a single bond or a divalent bridging group, R is $C_{1-4}$ alkyl or halo, m is 0-3 and n is from 2 to about 7.

In formula I, the $A^1$ value may have formula II in which each of $A^3$ and $A^4$ unsubstituted phenylene or a substituted derivative thereof. Unsubstituted phenylene radicals are preferred. Both $A^3$ and $A^4$ are preferably p-phenylene, although both may be o- or m-phenylene or one o- or m-phenylene and the other p-phenylene.

The Y value is a single bond or is a bridging radical in which, most often, one or two atoms, preferably one, separate $A^3$ from $A^4$. It is usually a hydrocarbon radical and particularly a saturated $C_{1-12}$ aliphatic or alicyclic radical such as methylene, cyclohexylmethylene, [2.2.1]bicycloheptylmethylene, ethylene, ethylidene, 2,2-propylidene, 2,2-dimethyl-1,1-propylidene, cyclohexylidene, cyclopentadecylidene, cyclododecylidene or 2,2-adamantylidene, especially an alkylidene radical. Aryl-substituted radicals are included, as are unsaturated radicals and radicals containing atoms other than carbon and hydrogen; e.g., oxy groups. Substituents such as those previously enumerated may be present on the aliphatic, alicyclic and aromatic portions of the Y group. Most preferably, Y is isopropylidene.

The $A^1$ radical may also have the spiro(bis)indane structure of formula III, in which R may be halo (e.g., chloro or bromo) or alkyl (e.g., methyl, ethyl, 2-propyl, n-butyl). Most often, the spiro(bis)indane is unsubstituted; i e., it is 6,6'-dihydroxy-3,3,3',3'-tetramethyl-1,1'-spiro(bis)indane, hereinafter sometimes designated "SBI". Also within the scope of the inventions are compositions comprising macrocyclic oligomers in which the $A^1$ radicals are a mixture of those of formulas II and III.

The $A^2$ value in any individual molecule of the compositions of the invention may be p-phenylene, m-phenylene or a mixture thereof. Of the total number of moieties in the composition, about 2-65%, preferably about 2-50% and most preferably about 5-30% are p-phenylene, with the remainder being m-phenylene. Within these limits, and especially the preferred limits, the levels of crystalline species are reduced, which results in a decrease in the melting temperature to below about 200° C. This has been shown by high pressure liquid chromatography to be at least in part a result of the presence of many macrocyclic molecular species, a relatively large number thereof being present in large proportions.

At higher levels of terephthalate species (in which $A^2$ is p-phenylene), the presence of increased amounts of linear polyarylates also contributes to the reduced crystallinity. Above 65 mole percent terephthalate species, however, formation of macrocyclic oligomers is not favored and linear polyarylates predominate; even above 50 mole percent, only about 50% (by weight) macrocyclics are formed.

The compositions of this invention may be prepared by the reaction of a mixture of isophthaloyl and terephthaloyl chlorides (hereinafter sometimes designated "acid chloride mixture") with at least one water-soluble salt of a dihydroxyaromatic compound of the formula HO-$A^3$-Y-$A^4$-OH, in the presence of at least one quaternary ammonium salt. The acid chloride mixture is employed in the form of a solution, preferably freshly prepared, in a substantially water-immiscible organic liquid, typically an aromatic hydrocarbon such as toluene or xylene; a substituted aromatic hydrocarbon such as chlorobenzene, o-dichlorobenzene or nitrobenzene; or a chlorinated aliphatic hydrocarbon such as chloroform, methylene chloride, trichloroethane or tetrachloroethane. The chlorinated aliphatic hydrocarbons, especially methylene chloride, are usually preferred.

The salt of the dihydroxyaromatic compound (hereinafter sometimes designated "bisphenol salt" for brevity) is employed in the form of an aqueous solution, also preferably freshly prepared. It is preferably an alkali metal salt, most often sodium or potassium and especially sodium.

In general, the preferred quaternary ammonium salts for use in the reaction are those described in the aforementioned U.S. Pat. No. 4,757,132. Said salt serves as a phase transfer catalyst. The preferred salts are those having a single alkyl group containing about 8-20 and preferably about 12-20 carbon atoms and having not more than five additional carbon atoms.

For the preparation of compositions of this invention wherein $A^1$ has formula II, the solutions of acid chloride mixture and of bisphenol salt are generally simultaneously introduced into a solution of the quaternary ammonium salt in the organic liquid. When $A^1$ has formula III, the bisphenol salt solution may be present in the reaction vessel. When a mixture of bisphenols is employed in which $A^1$ has both formulas, both modes of introduction may be used.

The amount of quaternary ammonium salt employed is most often about 1-5 mole percent based on acid chloride mixture, and the solution thereof generally contains about 0.5-5.0 grams of quaternary ammonium salt per liter of organic liquid. In terms of the proportion of acid chloride mixture with reference to total organic liquid, it is usually preferred to employ up to about 0.4 mole and especially about 0.1-0.3 mole per liter.

It is most often found that cyclic polyarylate yields are maximized if the amount of water employed to dissolve the bisphenol salt is low. Thus, a solution containing at least about 90% of the amount to provide a saturated solution is often preferred especially in the case of bisphenol A, and a saturated solution is most preferred. In the case of bisphenol A disodium salt, a saturated solution is about 0.78 $\underline{M}$.

Yields are also maximized by maintaining the reagents at low concentration in the reaction mixture, thus promoting intramolecular rather than intermolecular reaction. It is thus usually preferred to introduce a relatively concentrated solution of acid chloride mixture, together with the aqueous solution of bisphenol salt, into a vessel containing a relatively large amount of organic liquid. The solution of acid chloride mixture generally has a concentration of at least about 1.0-3.5$\underline{M}$.

The proportion of bisphenol salt employed is preferably at least about 3% in excess of stoichiometric; that is, at least about 3% greater than an equimolar amount with respect to acid chloride mixture. The presence of such an excess frequently improves the yield of cyclic polyarylates. It is generally not necessary to use more than about a 5% excess.

Reaction temperatures are not critical but are generally in the range of 0-100° C., most often about 25-100° C. An interesting feature of the preferred method described herein is that there is no apparent need to increase the temperature in order to obtain the desired cyclic polyarylates in high yields; therefore, methylene chloride may be employed as the organic liquid at temperatures below its boiling point (about 40° C.), and the cyclic products are nevertheless obtained in relatively high yield.

Following preparation of the cyclic polyarylates of this invention, it is possible to isolate them by conventional methods. Isolation can begin essentially immediately after addition of bisphenol salt and acid chloride mixture, since the reaction is substantially complete at that time.

If separation of the cyclic polyarylates from by-product linear polyarylate is desired, it may be achieved by precipitation from the organic liquid using a non-solvent such as acetone or tetrahydrofuran. It is sometimes found that the macrocyclic product contains very large proportions of trimers, which, as previously mentioned, may melt at a very high temperature. Said trimers usually precipitate as the mixture is allowed to stand at room temperature, or upon cooling. It is often advantageous to remove the precipitated fraction to improve processability of the compositions of this invention. However, removal of linear polyarylate is frequently not required.

The invention is illustrated by the following examples.

EXAMPLE 1

A three-necked, five-liter Morton flask equipped with a mechanical stirrer and condenser was charged with 1600 ml. of methylene chloride and 1.37 grams (3.75 mmol.) of hexadecyltrimethylammonium bromide. The solution was brought to reflux and there were simultaneously added over 30 minutes, with stirring, 500 ml. of a 0.78 $\underline{M}$ aqueous solution of bisphenol A disodium salt and 125 ml. of a 3 $\underline{M}$ solution in methylene chloride of isophthaloyl chloride and terephthaloyl chloride in a 4:1 weight ratio.

The mixture was separated into aqueous and organic layers and the organic layer was washed once with dilute aqueous hydrochloric acid solution and three times with water. A thick emulsion formed upon water washing; it was broken by filtration through silicone phase separation paper. Gel permeation chromatographic analysis of the organic phase indicated a 63% yield of macrocyclic oligomers.

The organic phase was added to 2.5 volumes of acetone, whereupon linear polyarylate and approximately 20% of the cyclics precipitated. Upon standing, further cyclics including a substantial proportion of the cyclic trimers also precipitated; said trimer mixture had a melting point of 404° C. The solids were removed by filtration.

The remaining cyclic polyarylate oligomers could be isolated by concentrating the organic solution, by precipitation with methanol or by steam crumbing. The macrocyclic polyarylate oligomer mixture thus obtained was completely melted at about 190° C.

EXAMPLE 2

A 5-necked, 250-ml. Morton flask equipped with a mechanical stirrer, reflux condenser and heating mantle was charged with 3.20 grams (10.4 mmol.) of 6,6'-dihydroxy -3,3,3',3'-tetramethyl-1,1'-spiro(bis)indane, 218 mg. (0.6 mmol.) of hexadecyltrimethylammonium bromide, 2.7 ml. of a 9.75 $\underline{M}$ aqueous sodium hydroxide solution and 100 ml. of methylene chloride. The mixture was heated to reflux and there were simultaneously added over 25-30 minutes, with stirring, 20 ml. of a 1 $\underline{M}$ solution in methylene chloride of isophthaloyl and terephthaloyl chlorides in equimolar amounts and 20 ml. of a solution of 11.86 grams (52 mmol.) of bisphenol A and 10.7 ml. of 9.75 $\underline{M}$ aqueous sodium hydroxide solution in enough water to produce a total volume of 100 ml. The milky solution slowly clarified as the reaction proceeded.

When the addition was complete, 50 ml. of water was added and the organic and aqueous phases were separated. The organic phase was washed with aqueous hydrochloric acid solution and with water, the phases were allowed to separate and the organic phase was removed and poured into 300 ml. of a 3:1 (by volume) mixture of acetone and methanol. The linear polyarylate precipitated and was removed by filtration. The organic phase was concentrated to yield 5 grams (63% of theoretical) of a macrocyclic polyarylate oligomer mixture (as determined by gel permeation chromatography) having a glass transition temperature of 222° C.

The macrocyclic polyarylate oligomers of this invention may be polymerized to linear polyarylates as described in the aforementioned U.S. Pat. No. 4,757,132. It has been found that linear polyarylates of very high molecular weights, frequently above 150,000 (weight average) as determined by gel permeation chromatography, can be prepared therefrom.

For example, upon solution mixing of the product of Example 1 with 0.1 mole percent (based on cyclic polyarylate structural units) of tetra-2-ethylhexyl titanate, stripping of solvent and heating of the residue at 300° C. for 15 minutes, there was obtained a linear polyarylate having a weight average molecular weight of 151,000. Similar products were obtained with 0.25 mole percent lithium salicylate and 0.1 mole percent aluminum tris-(acetylacetonate); the latter product also contained 8% (by weight) unconverted macrocyclic oligomers. Each linear polyarylate had a glass transition temperature of 187.C

What is claimed is:

1. A macrocyclic polyarylate oligomer composition comprising molecules of the formula

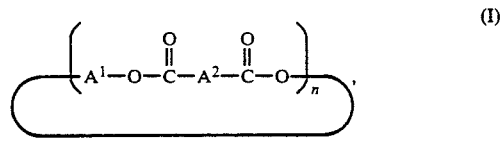   (I)

wherein $A^1$ is

   (II)

or

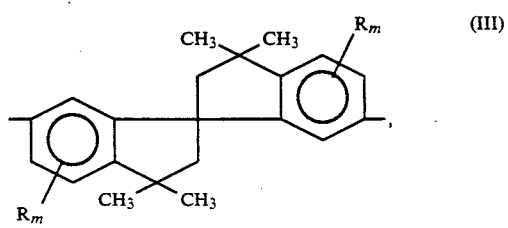   (III)

about 2-65% of the $A^2$ moieties are p-phenylene and the remainder are m-phenylene, each of $A^3$ and $A^4$ is unsubstituted or substituted phenylene, Y is a divalent bridging group, R is $C_{1-4}$ alkyl or halo, m is 0-3 and n is from 2 to about 7.

2. A composition according to claim 1 where $a^1$ has formula II.

3. A composition according to claim 2 wherein about 2-50% of the $A^2$ moieties are p-phenylene.

4. A composition according to claim 2 wherein about 5-30% of the $A^2$ moieties are p-phenylene.

5. A composition according to claim 4 where each of $A^3$ and $A^4$ is p-phenylene and Y is isopropylidene.

6. A composition according to claim 1 wherein $A^1$ has formula III.

7. A composition according to claim 6 wherein m is 0.

8. A composition according to claim 7 wherein about 2-50% of the $A^2$ moieties are p-phenylene.

9. A composition according to claim 7 wherein about 5-30% of the $A^2$ moieties are p-phenylene.

10. A composition according to claim 1 comprising a mixture of oligomers in which $A^1$ has formulas II and III.

11. A composition according to claim 10 wherein m is 0.

12. A composition according to claim 11 wherein about 2-50% of the $A^2$ moieties are p-phenylene.

13. A composition according to claim 11 wherein about 5-30% of the $A^2$ moieties are p-phenylene.

14. A composition according to claim 13 wherein each of $A^3$ and $A^4$ is p-phenylene and Y is isopropylidene.

* * * * *